US00PP19132P2

(12) United States Plant Patent
Kleinhanns

(10) Patent No.: US PP19,132 P2
(45) Date of Patent: Aug. 19, 2008

(54) ***PETUNIA* PLANT NAMED 'GLOW FLUOR ROSE'**

(50) Latin Name: *Petunia hybrida*
Varietal Denomination: Glow Flour Rose

(75) Inventor: Christoph E. Kleinhanns, Gernrode (DE)

(73) Assignee: Hamer Bloemzaden B.V., H.I. Ambacht (NL)

( * ) Notice: Subject to any disclaimer, the term of this patent is extended or adjusted under 35 U.S.C. 154(b) by 0 days.

(21) Appl. No.: 11/827,190

(22) Filed: Jul. 11, 2007

(51) Int. Cl.
*A01H 5/00* (2006.01)

(52) U.S. Cl. ..... Plt./356
(58) Field of Classification Search ..... Plt./356
See application file for complete search history.

*Primary Examiner*—Wendy C. Haas
(74) *Attorney, Agent, or Firm*—Jondle & Associates, P.C.

(57) ABSTRACT

A *petunia* cultivar particularly distinguished by early flowering, bright rose colored flowers, compact trailing habit and strong garden performance is disclosed.

2 Drawing Sheets

Genus and species: *Petunia hybrida.*
Variety denomination: 'Glow Fluor Rose'.

BACKGROUND OF THE NEW PLANT

The present invention comprises a new and distinct cultivar of *petunia,* botanically known as *Petunia hybrida,* and hereinafter referred to by the cultivar name 'Glow Fluor Rose'. 'Glow Fluor Rose' originated from a hybridization in May 2002 in Quedlinburg, Schsen-Anhalt, Germany. The female parent was a *petunia* with purple flowers while the male parent was a *petunia* with pink flowers.

The new cultivar was first propagated in summer of 2006 from mother stock and has been asexually reproduced through vegetative cuttings for five generations. The present invention has been found to retain its distinctive characteristics.

SUMMARY OF THE INVENTION

The following are the most outstanding and distinguishing characteristics of this new cultivar when grown under normal horticultural practices in Quedlinburg, Germany.

1. Bright rose flowers;
2. Early flowering;
3. Compact, trailing plant habit; and
4. Strong garden performance.

DESCRIPTION OF THE PHOTOGRAPHS

This new *petunia* plant is illustrated by the accompanying photographs which show blooms and foliage of the plant in full color, the colors shown being as true as can be reasonably obtained by conventional photographic procedures.

DESCRIPTION OF THE NEW CULTIVAR

Figure 1:
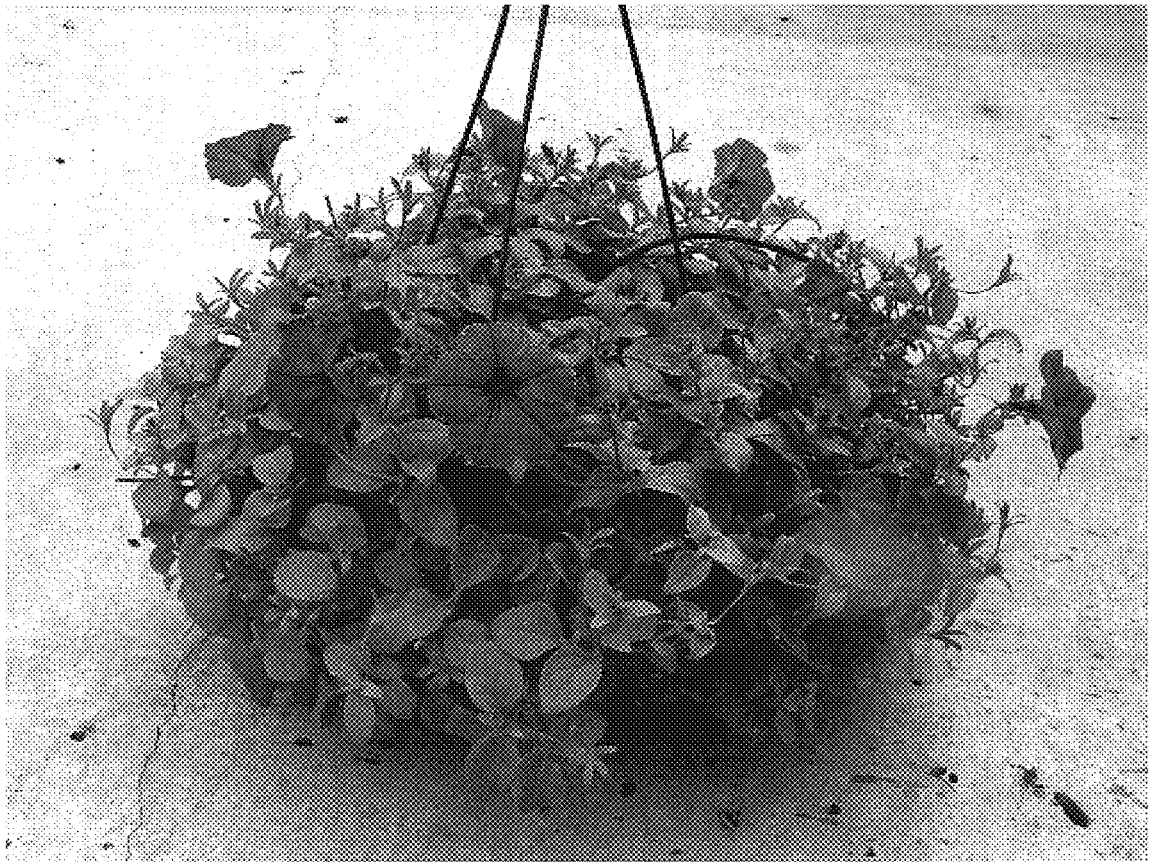
FIG. 1 shows the overall plant habit, including blooms, buds and foliage.
Figure 2:
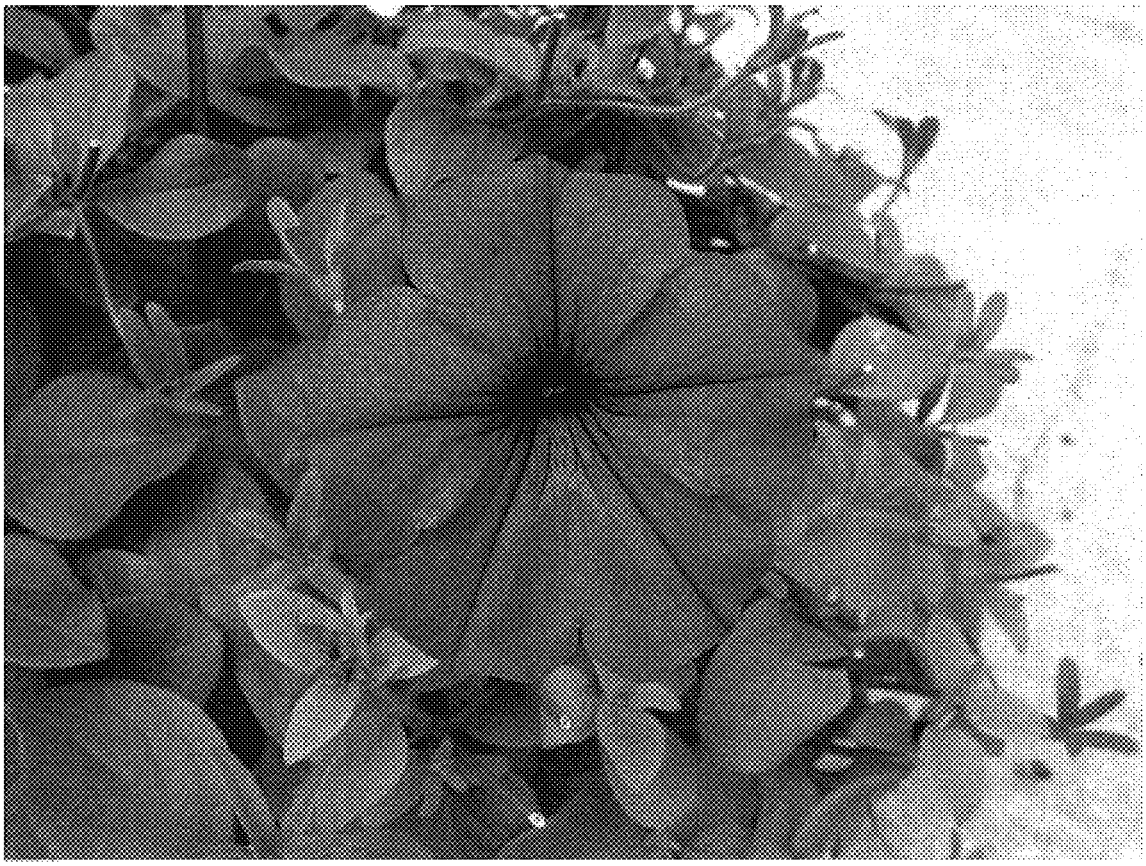
FIG. 2 shows the mature inflorescence.

The following detailed descriptions set forth the distinctive characteristics of 'Glow Fluor Rose'. The data which defines these characteristics were collected from asexual reproductions carried out in Quedlinburg, Sachsen-Anhalt, Germany. Data was collected on plants in 12 inch pots in October. Color references are primarily to the R.H.S. Colour Chart of The Royal Horticultural Society of London (R.H.S.) (4$^{th}$ ed). Anatomic labels are from *The Cambridge Illustrated Glossary of Botanical Terms,* by M. Hickey and C. King, Cambridge University Press.

DETAILED BOTANICAL DESCRIPTION

Classification:
- *Family.*—Solanaceae.
- *Botanical.*—*Petunia hybrida.*
- *Common name.*—*Petunia.*

Parentage:
- *Female parent.*—*Petunia* with purple flowers.
- *Male parent.*—*Petunia* with pink flowers.

Plant:
- *Form.*—Trailing.
- *Habit.*—Upright, later trailing.
- *Height.*—10.0 cm to 30.0 cm.
- *Width.*—Radius: 20.0 cm to 40.0 cm. Diameter: 40.0 cm to 80.0 cm.
- *Propagation.*—Terminal tip cuttings.
- *Time to produce a finished flowering plant.*—10 to 12 weeks.
- *Time to initiate and develop roots.*—4 to 5 weeks.
- *Root description.*—Fine rooting system, with white to light brown roots.

Stems:
- *Average number (basal).*—5 to 25.
- *Length of basal branches.*—40.0 cm to 70.0 cm.
- *Internode length.*—1.0 cm to 5.0 cm.
- *Diameter of branches from midpoint.*—Radius: 0.1 cm to 0.3 cm. Diameter: 0.2 cm to 0.6 cm.
- *Stem color.*—RHS 138B (Green).
- *Anthocyanin.*—Absent.
- *Texture.*—Pubescent.

Leaves:
- *Arrangement.*—Alternate.
- *Size.*—Length: 1.0 cm to 5.0 cm. Width: 0.5 cm to 3.0 cm.

*Shape.*—Oval to ovate, sometimes running spiky to the apex.

*Margin.*—Entire.

*Apex.*—Round to spiky.

*Base.*—Round running to the stem.

*Immature leaf.*—General color: RHS 131B (Dark green). Upper surface: RHS 138A (Dark green). Lower surface: RHS 138B (Lighter green). Texture: Pubescent.

*Mature leaf.*—General color: RHS 135A (Dark green). Upper surface: RHS 138A (Dark green). Lower surface: RHS 138B (Lighter green).

*Texture.*—Pubescent, mucilaginous.

*Venation.*—Nondistinct. Venation color: RHS 138C (Light green). Upper surface: RHS 138C (Light green). Lower surface: RHS 138C (Light green).

*Petioles.*—Leaves nearly direct on the branches.

Flower bud:

*Shape.*—Long tubular.

*Size.*—Length: 4.0 cm to 6.0 cm. Diameter: Radius: 0.1 cm to 0.3 cm. Diameter: 0.2 cm to 0.6 cm.

*Color at tight bud.*—RHS 86A (Dark violet).

*Immature flower color.*—RHS 148A (Dark violet to light violet).

Inflorescence:

*Blooming habit (flowering season).*—May to November.

*Inflorescence type.*—Single flowers.

*Number of flowers per node.*—1.

*Lastingness of individual blooms on the plant.*—About 7 days, but very much dependent on irrigation, fertilizer and temperature.

*Fragrance.*—Soft.

*Pedicels.*—Color: RHS 141C (Light green). Length: 1.0 cm to 4.0 cm. Diameter: Radius: Less than 0.1 cm to 0.15 cm. Diameter: 0.1 cm to 0.3 cm. Texture: Pubescent, soft.

Flowers:

*Shape.*—Funnel shaped.

*Size.*—Diameter (flower face): Radius: 2.5 cm to 3.5 cm. Diameter: 5.0 cm to 7.0 cm. Depth: 4.0 cm to 6.0 cm. Funnel: Length: 2.5 cm to 3.5 cm. Diameter: Radius: 0.3 cm to 0.6 cm. Diameter: 0.6 cm to 1.2 cm. Outside texture: Pubescent, RHS 86A (Dark violet).

*Mature flower.*—Face/Margin Color: RHS 80A (Light Violet). Upper surface: RHS N87A (Light violet). Lower surface: RHS N87B (Light violet). Corolla tube: Shape of corolla: Open, funnel shaped. Color inside (throat): RHS 86A (Dark violet). Color outside: RHS 86A (Dark violet). Petals: Apex: Round. Base: Fused. Margin: Entire. Waviness: Very soft. Lobation: Moderately lobed. Texture: Smooth.

*Calyx arrangement.*—Symmetric.

*Sepals.*—Number: 5. Color: RHS 142C (Light-green). Length: 1.0 cm to 2.5 cm. Width: 0.3 cm to 0.6 cm. Shape: Not fused, longish. Apex: Round. Base: Longish. Margin: Entire, not fused. Texture: Hairy.

Reproductive organs:

*Stamens.*—Quantity: 5. Shape: Cylindrical. Color: RHS 91D (White-violet). Filament length: 1.0 cm to 1.5 cm. Filament diameter: Radius: Less than 0.1 cm. Diameter: Less than 0.1 cm.

*Anther.*—Shape: Oval. Color: RHS 158D (Cream). Length: 0.2 cm to 0.4 cm. Diameter: Radius: 0.1 cm to 0.15 cm. Diameter: 0.2 cm to 0.3 cm.

*Pollen.*—Color: RHS 158D (Cream). Amount: Abundant.

*Pistils.*—Number: 1. Length: 1.5 cm to 2.5 cm. Diameter: Radius: Less than 0.1 cm. Diameter: Less than 0.1 cm. Stigma: Color: RHS 142B (Light green). Shape: Oval. Length: 0.1 cm to 0.2 cm. Diameter: Radius: 0.1 cm to 0.15 cm. Diameter: 0.2 cm to 0.3 cm. Style: Color: RHS 149D (Light green). Length: 1.4 cm to 2.3 cm. Diameter: Radius: Less than 0.1 cm. Diameter: Less than 0.1 cm. Shape: Long cylindrical.

Seeds:

*Color.*—RHS 175A (Dark orange-brown).

*Length.*—Less than 0.1 cm.

*Diameter.*—Radius: Less than 0.1 cm. Diameter: Less than 0.1 cm. Shape: Round.

Disease and insect resistance: Resistance and susceptibility is typical of the species.

COMPARISON WITH KNOWN CULTIVARS

'Glow Fluor Rose' differs from the female parent *petunia* plant in that the female parent has a more upright growth habit than 'Glow Fluor Rose'. Additionally, 'Glow Fluor Rose' has a bright rose flower color, while the female parent has a purple flower color.

'Glow Fluor Rose' differs from the male parent *petunia* plant in that the male parent has larger flowers than 'Glow Fluor Rose'. Additionally, 'Glow Fluor Rose' has a bright rose flower color, while the male parent has a pink flower color.

'Glow Fluor Rose' differs from commercial *petunia* variety 'SURFINIA Amethyst' (U.S. Plant Patent applied for) in that 'Glow Fluor Rose' has a more upright growth habit than 'SURFINIA Amethyst'. Additionally, 'Glow Fluor Rose' has a flower color of RHS 87A while 'SURFINIA Amethyst' has a flower color of RHS 82A.

I claim:

1. A new and distinct cultivar of *petunia* plant as described and shown herein.

* * * * *